United States Patent [19]

Dickinson

[11] 4,200,759
[45] Apr. 29, 1980

[54] PREPARATION OF IMIDAZO[2,1-a]ISOINDOLE COMPOUNDS

[75] Inventor: Robert A. Dickinson, Chateauguay, Canada

[73] Assignee: Delmar Chemicals, Limited, LaSalle, Canada

[21] Appl. No.: 926,407

[22] Filed: Jul. 20, 1978

[51] Int. Cl.$^2$ .............................................. C07D 487/04
[52] U.S. Cl. ..................... 548/324; 546/201; 260/326.1
[58] Field of Search ........................................ 548/324

[56] References Cited

U.S. PATENT DOCUMENTS

| | | | |
|---|---|---|---|
| 3,657,269 | 4/1972 | Houlihan | 548/324 |
| 3,699,119 | 10/1972 | Eberle et al. | 548/324 |
| 3,803,155 | 4/1974 | Sulkowski et al. | 548/324 |
| 3,929,766 | 12/1975 | Metlesics et al. | 548/324 |
| 3,987,183 | 10/1976 | Anderson | 548/324 |

FOREIGN PATENT DOCUMENTS

| | | | |
|---|---|---|---|
| 1225411 | 3/1971 | United Kingdom | 548/324 |
| 1225412 | 3/1971 | United Kingdom | 548/324 |
| 1225413 | 3/1971 | United Kingdom | 548/324 |

OTHER PUBLICATIONS

Graf et al., Helv. Chim. Acta 1959, vol. 42, pp. 1085-1101.

Meerwein, Org. Synthesis, vol. V, 1973, pp. 1080-1082.
Aeberli et al., J. Med. Chem. 1975, vol. 18, pp. 177-182.

*Primary Examiner*—Alan L. Rotman
*Assistant Examiner*—Natalia Harkaway
*Attorney, Agent, or Firm*—Fisher, Christen & Sabol

[57] ABSTRACT

The present invention relates to a process for the preparation of certain known imidazo[2,1-a]isoindoles of the general formula I:

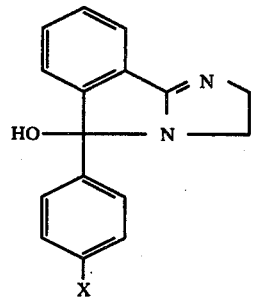

wherein X represents a hydrogen atom, a halogen atom or a lower alkoxy group. The said isoindoles, which may be prepared from novel lactams, have been shown to have utility as psychic energizers and anorectics.

34 Claims, No Drawings

PREPARATION OF IMIDAZO[2,1-a]ISOINDOLE COMPOUNDS

BACKGROUND OF INVENTION (a) Field of Invention

The present invention relates generally to a novel process for making certain known biologically active heterocyclic benzamide compounds. More particularly, the present invention is concerned with a novel process for producing imidazo[2,1-a]isoindoles of the general formula I:

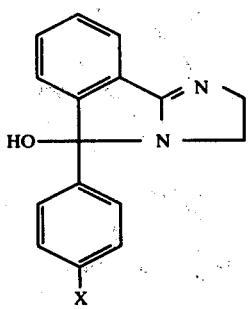

wherein X represents hydrogen, halogen in particular fluorine, chlorine and bromine, or lower alkoxy.

(b) Description of Prior Art

Imidazo[2,1-a]isoindoles of the general formula I and processes for their production are generally described, for example, in U. K. specifications Nos. 1,225,411 1,225,412 and 1,225,413.

In these specifications such imidazo [2,1-a] isoindoles are described as being biologically active and are indicated as having utility as psychic energizers and anorectics. Probably the best known of such compounds at the present time is 5-(p-chlorophenyl)-2,3-dihydro-5-hydroxy- 5H-imidazo[2,1-a]isoindole commonly referred to as mazindol.

The prior art discloses several processes for obtaining the compounds of formula I but these processes all leave something to be desired. For example, the processes disclosed in the above specification usually involve the reduction of an intermediate carbonyl compound followed by a very delicate oxidation. The process steps, and especially the latter, are very time consuming. Although the specifications teach that the oxidation step may be effected within a relatively short time by bubbling air or oxygen it should be noticed that the specifications emphasize, and all but one of the detailed specific examples illustrate, a very mild oxidation wherein the reaction mixture is merely contacted with air over a period of many, usually six, days. Since the simple procedure of bubbling a gas, especially air, through a reaction mixture generally presents few problems, the emphasis on the use of the very long oxidation step indicates that this procedure is highly preferred. The above processes also utilize lithium aluminum hydride as the agent to reduce the intermediate carbonyl function. This reagent is very expensive and, moreover, presents a significant fire hazard which, on a small scale, may be acceptable. However, the use of that reagent on a large, i.e. commercial, scale is very hazardous and involves significant inconvenience and expense. It may also be noted that the above specifications refer to process yields only in general terms and as being "appreciable". There is no specific yield given in any of the said three specifications and, although a much later reference (J. Med. Chem. 18, 177, (1975)) indicates that a yield of 65% is possible for the oxidation step, the present Applicant did not obtain a yield of even half that amount using the same process.

STATEMENT OF THE INVENTION

An object of the present invention is to provide an improved process for producing the compounds of formula I which process avoids the significant disadvantages of the prior art processes.

According to the present invention there is provided a process for making imidazo[2,1-a]isoindoles of the general formula I:

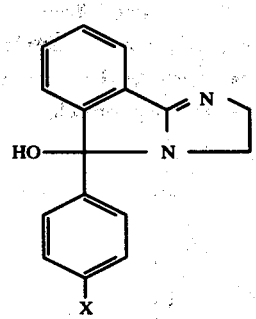

wherein X represents hydrogen, halogen in particular fluorine, chlorine and bromine or lower alkoxy, comprising reacting, optionally under an inert gas, for example, nitrogen, atmosphere and/or in the presence of a solvent, for example, methylene chloride a compound of formula II.

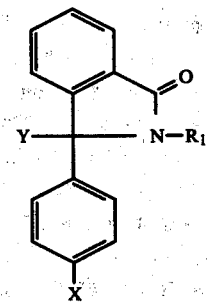

wherein
$R_1$ is lower alkyl;
X is as defined above; and
Y is $-NR_2R_3$ or $-O-R_4$ wherein $R_2$, $R_3$ and $R_4$ are individually lower alkyl or aryl or $R_2$ and $R_3$ together represent an alkylene chain of formula $-(CH_2)-_n$ wherein n is 4, 5 or 6 with an alkylating agent selected from the group consisting of oxonium salts of the formula (R) $_3O^+Z^-$ and carbonium salts of the formula:

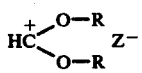

wherein
R is methyl or ethyl; and
$Z^-$ is the fluoroborate, hexachloroantimonate or hexafluorophosphate ion, to form a corresponding salt of formula

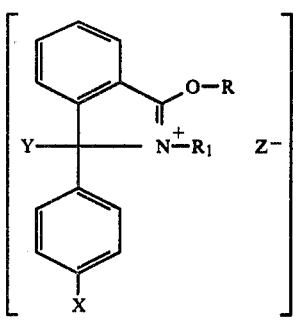

III

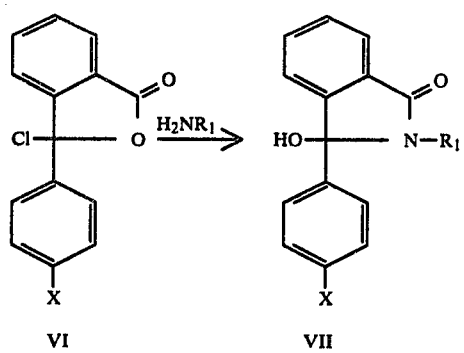

-continued

VI    VII reacting under an inert gas, for example, nitrogen, atmosphere and/or in the presence of a solvent, for example, methylene chloride said salt with ethylene diamine to form an intermediate represented by formula IV:

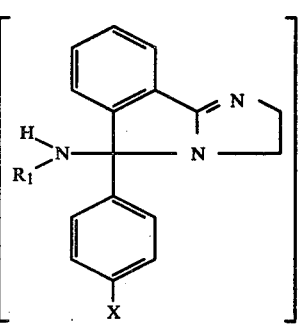

IV

IIa    VIII which compound is hydrolysed in the presence of an acid to form the desired compound of formula I. The above reactions in methylene chloride may be effected at temperatures up to reflux of the reaction medium.

Compounds of formulas I through IV, wherein X=Cl, are designed Ib, IIc, IIIa and IVa, respectively.

The dialkylamino lactams of formula IIa below used as starting materials in the process of the present invention are novel compounds and constitute a further aspect of the present invention. They and the alkoxy lactams of formula IIb may be conveniently obtained from the corresponding benzoyl benzoic acid derivatives, for example, as follows:

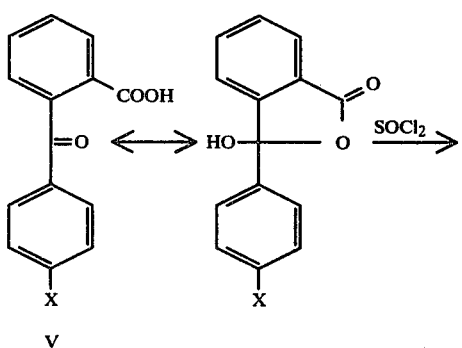

V

IIb wherein $R_1$, $R_2$, $R_3$, $R_4$ and X are as defined above.

The benzoyl benzoic acid derivatives of formula V are readily available (refer for example to W. Graf, E. Girod, E. Schmid and W. G. Stoll, *Helv. Chim. Acta*, 42, 1085 (1959)). As an example, 2-(4'-chlorobenzoyl)benzoic acid required as starting material in the production of mazindol is readily produced by the reaction of chlorobenzene with phthalic anhydride.

The present invention will be further described with reference to the following specific examples but is not to be considered as limited thereto.

EXAMPLES 1–6

These examples illustrate the preparation of specific compounds of formula I utilizing the novel compounds of formula II. Examples 1–5 illustrate the production of the preferred compound mazindol.

EXAMPLE 1

Preparation of Mazindol from
Dimethylamino-Lactam—Formula IIa: $R_1=CH_3$;
$R_2=R_3=CH_3$; $X=Cl$ Crystalline dimethylamino lactam IIa (60 g; 0.20 mole) was added to a solution of 48 g (0.25 mole) of triethyloxonium fluoroborate (the triethyloxonium fluoroborate was prepared in situ—ref. H. Meerwein, Org. Synthesis, Coll. Vol. V, 1080 (1973) in 80 ml of dry methylene chloride. The mixture was stirred at reflux under nitrogen for 5 hours, cooled to 0° and 30.6 g (0.51 mole) of ethylene diamine added over 30 minutes. This mixture was refluxed under nitrogen for 5 hours, cooled to 5° and made strongly acidic by the careful addition of 200 ml of 4N aqueous hydrochloric acid. After 3 hours of reflux at 40° the methylene chloride was removed by distillation, and then the mixture was basified (pH 8.0—8.5) with 45 ml of 50% W/V sodium hydroxide. The voluminous white precipitate which formed was filtered and washed with two 100 ml portions of water. After drying at 25° 64 g of crude product was obtained. Recrystallization from methanol-methylene chloride (1:1) followed by suspension at reflux in the same solvent system yielded 35.3 g (62% theoretical from dimethylamino lactam IIa) of pure mazindol m.p. 201-202° with a setting of 6.5 in the Thompson-Hoover capillary melting point apparatus (lit. 201-202° under similar conditions ref. P. Aeberli et al, J. Med. Chem. 18 p. 177 (1975)).

| Analysis: | %C | %H | %N | %Cl | %O |
|---|---|---|---|---|---|
| Calculated | 67.49 | 4.60 | 9.84 | 12.45 | 5.62 |
| Found | 67.25 | 4.69 | 9.74 | 12.42 | 5.62 |

EXAMPLE 2

Preparation of Mazindol from Pyrrolidinyl
Lactam—Formula IIa: $R_1=CH_3$; $R_2$ with $R_3$
$=-(CH_2)_4-$; $X=Cl$ The pyrrolidinyl lactam (2.0 g; 6.1 mM) dissolved in dry methylene chloride (3 ml) was added to triethyloxonium fluoroborate (prepared as in Example 1) (2.4 g; 13 mM) in methylene chloride (3 ml) and the mixture refluxed under nitrogen for 5 hours. After cooling to 0°, ethylene diamine (3.6 g; 60 mM) was added and this mixture refluxed under nitrogen for 5 hours, and then stirred for 18 hours at 25°. Aqueous hydrochloric acid was added until the solution was strongly acidic (10 ml of 4NHCl) and the resulting mixture refluxed for 3 hours. After cooling, aqueous sodium hydroxide was added until the pH was 7.5-8.5 (~10 ml 20% NaOH) and a large amount of white precipitate was observed. The reaction mixture was stirred at 0° for 30 minutes, filtered and the filtrate washed with cold water. The so-obtained crude mazindol was dried at 60° for 18 hours and then recrystallized from methanol to give 0.8 g (46% theoretical) of pure mazindol characterized as in Example 1.

EXAMPLE 3

Preparation of Mazindol from Piperidinyl
Lactam—Formula IIa: $R_1=CH_3$; $R_2$ with
$R_3=-(CH_2)_5$; $X=Cl$ A solution of 1.0 g (2.9 mM) of said lactam dissolved in 5 ml dry methylene chloride was added to 2.4 g (13 mM) of triethyloxonium fluoroborate (prepared as in Example 1) dissolved in 2 ml of dry methylene chloride. The mixture was refluxed under nitrogen for 5 hours and then cooled in an ice bath. Ethylene diamine (3 g; 50 mM) was added dropwise over 10 minutes and the mixture refluxed under nitrogen for 18 hours. After cooling the mixture to 25° aqueous hydrochloric acid (15 ml of 10% HCl) was added and the acidic mixture (pH≃1) refluxed for 4 hours. Upon basification of the resulting solution with aqueous sodium hydroxide (15 ml of 10% NaOH) a voluminous white precipitate separates. The whole mixture was stirred in an ice bath for 20 minutes, filtered and washed well with cold water. After air-drying, the precipitate was suspended in cold ether, filtered and washed with cold ether to give 250 mg (30% theoretical) of crystalline mazindol shown by comparison to be the same product as obtained in Example 1).

EXAMPLE 4

Preparation of Mazindol from Dimethylamino
Lactam—Formula IIa: $R_1=CH_3$; $R_2=R_3=CH_3$;
$X=Cl$ Using Dimethoxycarbonium Fluoroborate
$((CH_3O)_2CH^+ {}^{BF_4-})$ Dimethoxycarbonium fluoroborate (5 g : 31 mM) prepared in situ according to R. F. Borch, J. Org. Chem., 34, 627 (1969) was suspended in 10 ml of methylene chloride under an atmosphere of nitrogen and 3 g (10 mM) of said dimethylamino lactam added thereto. The mixture was stirred at room temperature for 18 hours; the resulting yellow solution was cooled to 0° and 6.3 g (105 mM) of ethylene diamine was added over 15 minutes. This mixture was refluxed for 5 hours, recooled to 0°; 20 ml of 4N aqueous hydrochloric acid was added and the mixture refluxed at 40° for 5 hours. After cooling, the mixture was partitioned and the organic fraction washed with 10 ml of 2N aqueous hydrochloric acid. This aqueous wash liquor was combined with the previous aqueous layer and the mixture basified (pH≃9.0) with 10 ml of 50% sodium hydroxide. A precipitate resulted which was collected by filtration, washed with 20 ml of water and dried at 25°. The crude product was suspended in ethyl acetate; filtered and washed with cold ethyl acetate to give 450 mg (16%) of crystalline mazindol evaluated to be pure by comparison as previously.

EXAMPLE 5

Preparation of Mazindol from Methoxy
Lactam—Formula IIb: $R_4=R_1=CH_3$; $X=Cl$

A solution of 500 mg. (1.7 mM) of the methoxy lactam dissolved in 5 ml of dry methylene chloride was added to a solution of 370 mg (1.9 mM) of triethyloxonium fluoroborate in 2 ml of dry methylene chloride maintained under an atmosphere of nitrogen. The mixture was stirred at room temperature under nitrogen for 18 hours and then the resulting yellow solution (containing the corresponding methoxy imidate salt) was added over 15 minutes to a solution of 2 g (33 mM) of ethylene diamine in 10 ml of methylene chloride kept at 0°. This mixture was stirred at room temperature for 48 hours and then acidified strongly by the addition of 5% aqueous hydrochloric acid (50 ml). The mixture was refluxed at 40° for 5 hours and then partitioned. The organic layer was washed with 10 ml of 5% aqueous hydrochloric acid and the combined aqueous layers were basified (pH=8.0-8.5) by the addition of 5 ml of 50% W/V sodium hydroxide. A precipitate resulted which was removed by filtration, washed with 20 ml of water and dried at 60°. The crude product was then suspended in cold ether, filtered and washed with cold ether to give 85 mg (17%) of crystalline mazindol, the product being characterized as previously.

EXAMPLE 6

Preparation of 5-Phenyl-2,3-Dihydro-5-Hydroxy-5H-Imidazo[2,1a]isoindole from Dimethylamino Lactam—Formula IIa: $R_1=C_2H_5$; $R_2=R_3=CH_3$; $X=H$ Triethyloxonium fluoroborate (12 g; 63 mM) (prepared as in Example 1) was dissolved in 7 ml of dry methylene chloride. A solution of 7.2 g (26 mM) of the dimethylamino-lactam in 10 ml of methylene chloride was added and the mixture stirred at reflux under nitrogen for 5 hours. After cooling to 0°, 20 g (330 mM) of ethylene diamine was added over 15 minutes and the mixture stirred under $N_2$ at room temperature for 18 hours. The mixture was cooled to 0° and made strongly acidic with 80 ml of 4N aqueous hydrochloric acid. Following heating at reflux for 3 hours the mixture was cooled and then made basic by the addition of 10% aqueous sodium hydroxide. The voluminous white precipitate thus formed was filtered and washed twice with cold water. The crude product was dried at 60° and then recrystallized from methanol to give 4.4 g (68% theoretical) of the desired product in pure state, m.p. 200–202° (lit. 202–203°—P. Aeberli et al, *J. Med. Chem.* 18, 177 (1975).

The following examples illustrate the production of the preferred compound mazindol using a alkylating agent triethyloxonium hexachloroantimonate and triethyloxonium hexafluorophosphate, respectively. The experiments were effected purely to demonstrate the use of alternative alkylating agents and no attempts were made to optimize reaction conditions, yield, etc.

EXAMPLE 7

Preparation of Mazindol from Dimethylamino Lactam—Formula IIa: $R_1=CH_3$; $R_2=R_3=CH_3$; $X=CL$—Using Triethyloxonium Hexachloroantimonate $((C_2H_5)_3O^+SbCl_6^-)$ Crystalline dimethylamino lactam IIa (6.4 g; 21.4 mM) was dissolved in 12 ml of dry methylene chloride and added at room temperature to a suspension of 11.9 g (27.2 mM) of triethyloxoniumhexachloroantimonate in 12 ml of dry methylene chloride. The mixture was stirred at reflux under nitrogen for 3 hours, cooled at 5° and 3.3 g (55 mM) of ethylene diamine added over 5 minutes. The mixture was then refluxed under nitrogen for 5 hours, cooled to 5° and made strongly acidic by the addition of 20 ml of 4 N aqueous hydrochloric acid. After a 2 hour reflux period the mixture was cooled and basified with aqueous sodium hydroxide (13 ml of 25% NaOH). The resulting light yellow solid was collected by filtration from the two-phase system after a 30 minute cooling period at 0°. This crude mazindol was dried at 60° and then recrystallized from methanol-methylene chloride (1:1) to yield 0.7 g (11.5% theoretical) of white crystalline mazindol shown by comparison to be the same product as obtained in Example 1.

EXAMPLE 8

Preparation of Mazindol from Dimethylamino Lactam—Formula IIa: $R_1=CH_3$; $R_2=R_3CH_3$; $X=Cl$—Using Triethyloxonium Hexafluorophosphate $((C_2H_5)_3O^+PF_6^-)$ A solution of 9.3 g (31 mM) of dimethylamino lactam IIa in 12 ml of dry methylene chloride was added at room temperature to a solution of 9.8 g (40 mM) of triethyloxonium hexafluorophosphate. The mixture was heated at reflux under nitrogen for 5 hours and then at room temperature for an additional 16 hours. After cooling to 0°, 4.8 g (80 mM) of ethylene diamine was added over a 15 minute period. The mixture was then refluxed under nitrogen for 5 hours, cooled to 5° and made acidic with 34 ml of 4 N aqueous hydrochloric acid. After another reflux period of 15 minutes the mixture was stirred at room temperature for 16 hours. Upon basification with aqueous sodium hydroxide (25 ml of 25% NaOH) a voluminous white precipitate separated. After cooling to 5° for 30 minutes the white solid was collected by filtration. The crude product was dried at 60° and then recrystallized from methanol-methylene chloride (1:1) to give 2.6 g (29% (theoretical) of crystalline mazindol shown by comparison to be the same product as obtained in Example 1.

The following examples illustrate the preparation of the novel lactams of formula II:

EXAMPLE 9a

Preparation of Pseudo Acid Chloride—Formula VI—$X=H$

To a solution of 55.3 g (0.47 mM) of thionyl chloride in 100 ml of chloroform was added 100 g (0.44 mM) of o-benzoyl benzoic acid (V) and the mixture heated at reflux for 2 hours. Excess thionyl chloride and solvent was removed at reduced pressure to give 108 g (100% theoretical) of crude acid chloride VI. This material is used in subsequent reaction steps without further purification.

EXAMPLE 9b

Preparation of Hydroxy Lactam—Formula VII—$R_1=-C_2H_5$; $X=H$

A mixture of 110 ml of a 70% aqueous ethylamine (~1.7 mM of amine) and 100 ml of dioxan was prepared and cooled to 0°. A solution of 24.5 g (0.10 mM) of crude acid chloride VI (from 9a) in 50 ml of chloroform was added thereto dropwise over 30 minutes. The resulting mixture was stirred at room temperature for 30 minutes and then all the solvents are removed at reduced pressure with warming. The crude solid remaining was recrystallized from benzene to give 19.9 g (79% theoretical) of white crystalline hydroxy-lactam VII, m.p. 167°–169° (lit. 168°–170°, W. Graf, E. Girod, E. Schmid & W. G. Stoll, *Helv. Chim. Acta*, 42, 1085 (1959)).

EXAMPLE 9c

Preparation of Dimethylamino-Lactam—Formula IIa—$R_1=-C_2H_5$; $R_2=R_3=CH_3$ $X=H$ To 15 ml of thionyl chloride was added portionwise over 20 minutes 10 g (39.5 mM) of hydroxy-lactam VII from (9b). The solution was allowed to stand at room temperature for 30 minutes and then the excess thionyl chloride was removed at reduced pressure. The resulting crude solid chloro-lactam VIII was dissolved in 20 ml of chloroform and that solution added to 30 ml of chloroform which had been saturated with dimethylamine gas. After standing for 10 minutes, the mixture was washed with water and the organic layer dried over sodium sulfate. Removal of the solvent at reduced pressure yielded crude crystalline material which was suspended in hexane and then filtered to give 7.8 g (70% theoretical) of white crystalline dimethylamino-lactam IIa, m.p. 116°–117°.

EXAMPLE 10a-b

Preparation of Pseudo Acid Chloride—Formula VI—X=Cl and its Conversion to the Corresponding Hydroxy-Lactam of Formula VII—$R_1$=$CH_3$; X=Cl To a suspension of 100 g (0.38 mole) of 2-(p-chlorobenzoyl)benzoic acid (V) and 2 g of dimethyl formamide in 250 ml of methylene chloride was added over a period of 15 minutes 51.2 g (0.43 mole) of thionyl chloride. The mixture was heated carefully to reflux and stirred at reflux for 3 hours resulting in the solution of the intermediate acid chloride VI. This solution was cooled to room temperature and added over 20 minutes at 0° to 100 g of a 40% aqueous solution of methylamine (1.29 mole of amine). The mixture was stirred at room temperature for 1 hour, recooled to 0° and then made acidic with 6 N aqueous hydrochloric acid (150 ml). Most of the methylene chloride was evaporated whereupon the product crystallized out. The crystals so obtained were filtered, washed with cold water and dried at 60° to give 102 g (97% theoretical) of the hydroxy-lactam VII, m.p. 190°–194° (lit. 196°–199.5°, W. Graf, E. Girod, E. Schmid & W. G. Stoll, *Helv. Chim. Acta*, 42, 1085 (1959)).

EXAMPLE 10c(i)

Preparation of Dimethylamino-Lactam of Formula IIa—$R_1$=$CH_3$; $R_2$=$R_3$=$CH_3$; X=Cl To a suspension of 46 g (0.17 mole) of hydroxy-lactam VII (from 10b) in 140 ml of methylene chloride at 0° was added over 20 minutes, 24 g (0.20 mole) of thionyl chloride. Towards the end of the addition, a solution was obtained which was warmed to 25°, stirred for 1 hour and then recooled to 10°. To this solution (of chloro-lactam VIII) a stream of gaseous dimethylamine was introduced over a period of 15–20 minutes. The resulting mixture was washed twice with 50 ml portions of water and the organic layer was dried with sodium sulfate. The solvent and excess amine were removed at reduced pressure to yield a crude oily product. Trituration with cyclohexane gave 45 g (89%) of excellent crystalline dimethylamino lactam II, m.p. 111°–112°.

EXAMPLE 10c(ii)

Preparation of Pyrrolidinyl-Lactam of Formula IIa—$R_1$=$CH_3$; $R_2$ with $R_3$=—$(CH_2)_4$; X=Cl To 10 ml of thionyl chloride was added portionwise 2 g (7.3 mole) of solid hydroxy-lactam VII (from 10b) and the mixture allowed to stand for 10 minutes at room temperature. Excess thionyl chloride was then removed at reduced pressure to yield crude solid chloro-lactam VIII which was dissolved in 10 ml of chloroform and 1.3 g (18 mole) of pyrrolidine in 5 ml of chloroform added. The resulting mixture was stirred at room temperature for 10 minutes and then washed with 10 ml of water. The organic layer was dried over sodium sulfate and the solvent was removed at reduced pressure to yield 2.2 g (92% theoretical) of the pyrrolidinyl lactam as an oil. This material was used for the preparation of mazindol without further purification.

EXAMPLE 10c(iii)

Preparation of Piperidinyl-Lactam of Formula IIa—$R_1$=$CH_3$; $R_2$ with $R_3$=—$(CH_2)_5$—; X=Cl To 6 ml of thionyl chloride was carefully added 1.0 g (3.7 mole) of solid hydroxy-lactam VII (from 10b). The mixture was maintained at room temperature for one hour and then the excess thionyl chloride removed at reduced pressure to give crude solid chloro-lactam VIII which was dissolved in 5 ml of methylene chloride and 1.0 g (12 mole) of piperidine added thereto. After standing for 10 minutes at room temperature, the mixture was washed with 5 ml of water and the organic fraction dried over sodium sulfate. Removal of the solvent at reduced pressure gave 1.2 g (96% theoretical) of oily piperidinyl lactam II. This material was used directly in the preparation of mazindol without further purification.

EXAMPLE 11

Preparation of MethoxyLactam—Formula IIb—$R_1$=$R_4$=$CH_3$; X=Cl

10 G (36.5 mM) of solid hydroxy lactam formula VII (from 10b) was added portionwise over 15 minutes with external cooling to 25 g (210 mM) of thionyl chloride. After completion of the addition the mixture was stirred for a further 20 minutes at room temperature. The excess thionyl chloride was removed at reduced pressure to give crude solid chloro-lactam (Formula VIII-—$R_1$=$CH_3$; X=Cl). To the solid mass was carefully added 50 ml of methanol and the resulting solution was stirred at room temperature for one hour. The excess methanol was removed at reduced pressure and the residue was triturated with chloroform to yield 9.6 g (91% theoretical based on the hydroxy lactam VII) of crystalline methoxy lactam IIb, m.p. 83°–85° (m.p. 83°–85°—W. Graf, E. Girod, E. Schmid & W. G. Stoll, *Helv. Chim. Acta* 42 1085 (1959)). This material was used in the preparation of mazindol (refer Example 5) without further purification.

Throughout this text the term "lower" refers to organic moieties containing at most 6, and preferably at most 3, carbon atoms, and "aryl" preferably refers to the phenyl moiety.

The present invention provides a process which utilizes readily available materials and avoids the use of an expensive and hazardous reducing agent. Moreover, the process of the present invention generally provides product yields which compare very favourably with those obtained in the prior art processes.

What we claim is:

1. Process for the preparation of an imidazo [2,1-a] insoindole of formula I:

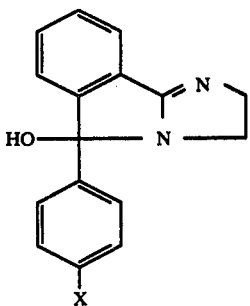

wherein X is hydrogen, halogen or lower alkoxy, comprising (a) reacting a compound of formula II:

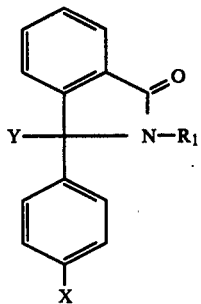

wherein $R_1$ is lower alkyl, X is as defined above, and Y is $NR_2R_3$ or $-O-R_4$, wherein $R_2$, $R_3$ and $R_4$ are individually lower alkyl or $R_2$ and $R_3$ together are an alkylene chain of formula $-(CH_2)_n-$ wherein n is 4, 5 or 6; with an alkylating agent selected from the group consisting of an oxonium salt of the formula:

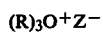

and a carbonium salt of the formula:

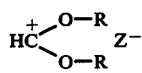

in which formulae R is methyl or ethyl, and $Z^-$ is the fluoroborate, hexachloroantimonate or hexafluorophosphate ion, to form a corresponding salt of formula III:

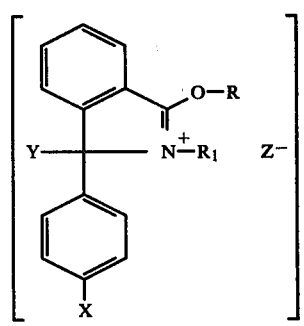

(b) reacting said salt with ethylene diamine to form an intermediate of formula IV:

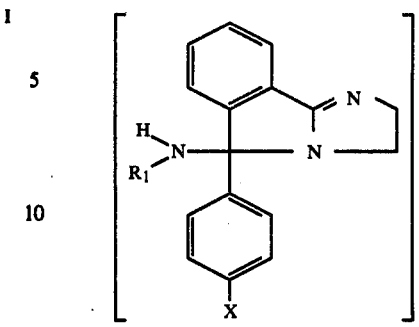

and (c) hydrolyzing said compound of formula IV to form the compound of formula I.

2. The process as claimed in claim 1 wherein the compound of formula II is alkylated under an inert gas atmosphere.

3. The process as claimed in claim 2 wherein the said inert gas atmosphere comprises nitrogen.

4. The process as claimed in claim 1 wherein the compound of formula III is reacted with ethylene diamine under an inert gas atmosphere.

5. The process as claimed in claim 2 wherein the compound of formula III is reacted with ethylene diamine under an inert gas atmosphere.

6. The process as claimed in claim 3 or 5 wherein said inert gas atmosphere comprises nitrogen.

7. The process as claimed in claim 5 wherein X is fluorine, chlorine or bromine.

8. The process as claimed in claim 5 wherein X is chlorine.

9. The process as claimed in claim 5 wherein the alkylation of the compound of formula II is effected in the presence of an inert organic solvent.

10. The process as claimed in claim 5 wherein alkylation of the compound of formula II is effected in the presence of methylene chloride.

11. The process as claimed in claim 5 wherein the alkylation of the compound of formula II is effected in the presence of methylene chloride and at a temperature up to the reflux temperature thereof.

12. The process as claimed in claim 5 wherein the reaction of the compound of formula III with ethylene diamine is effected in the presence of an inert organic solvent.

13. The process as claimed in claim 5 wherein the reaction of the compound of formula III with ethylene diamine is effected in the presence of methylene chloride.

14. The process as claimed in claim 5 wherein the reaction of the compound of formula III with ethylene diamine is effected in the presence of methylene chloride and at a temperature up to the reflux temperature thereof.

15. The process as claimed in claim 5 wherein the alkylation of the compound of formula II is effected with triethyloxonium fluoroborate.

16. The process as claimed in claim 5 wherein the alkylation of the compound of formula II is effected with dimethyoxycarbonium fluoroborate.

17. Process for the preparation of an imidazo [2,1-a] isoindole of formula I:

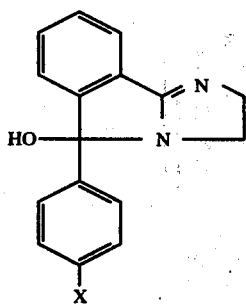

wherein X is hydrogen, halogen or lower alkoxy; comprising (a) reacting a compound of formula VIII:

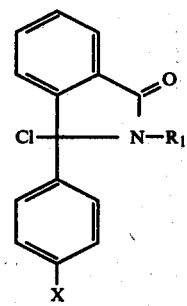

VIII where $R_1$ is lower alkyl; and X is as defined above; with (i) an amine of formula $HNR_2R_3$ in which $R_2$ and $R_3$ are individually lower alkyl or together are an alkylene chain of formula $-(CH_2)_n-$ wherein n is 4, 5 or 6 to form an amino lactam compound of formula II; or (ii) an alcohol of formula $R_4$—OH wherein $R_4$ is lower alkyl or whereby an alkoxy lactam of formula II is obtained;

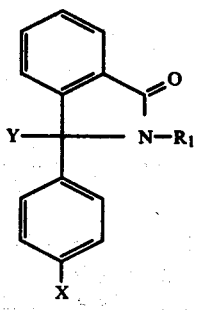

II wherein $R_1$ and X are as defined above and Y is $NR_2R_3$ or $-O-R_4$, wherein $R_2$, $R_3$ and $R_4$ are as defined above;

(b) reacting said compound of formula II with an alkylating agent selected from the group consisting of an oxonium salt of the formula:

$(R)_3O^+Z^-$ and a carbonium salt of the formula:

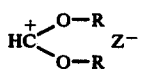

in which formulae R is methyl or ethyl, and $Z^-$ is the fluoroborate, hexachloroantimonate or hexafluorophosphate ion, to form a corresponding salt of formula III:

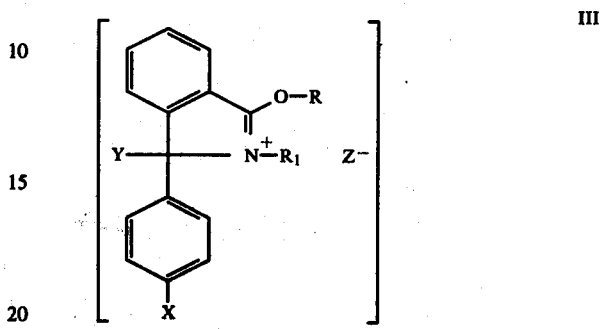

III (i) reacting said salt with ethylene diamine to form an intermediate of formula IV:

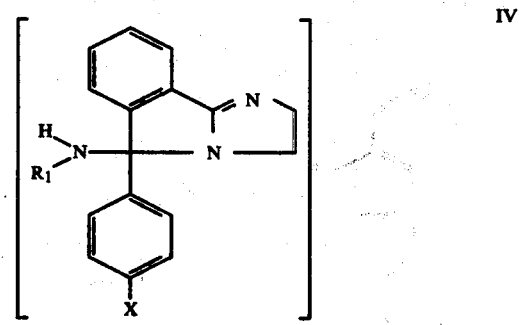

IV and (d) hydrolysing said compound of formula IV to form the compound of formula I.

18. Process for the preparation of an imidazo [2,1-a] isoindole of formula I:

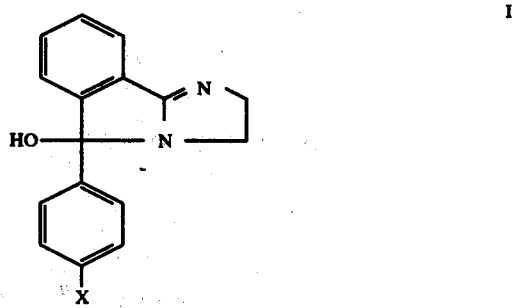

I wherein X is hydrogen, halogen or lower alkoxy; comprising (a) reacting a compound of formula VIII:

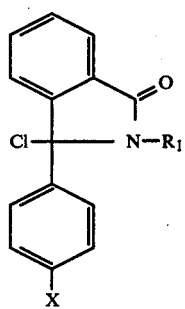

wherein $R_1$ is lower alkyl, and X is as defined above; with an amine of formula:

HNR_2R_3 wherein $R_2$ and $R_3$ are individually lower alkyl or together are an alklylene chain of formula —$(CH_2)_n$— wherein n is 4, 5 or 6; to form an amino lactum compound of formula II:

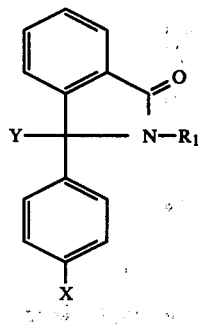

wherein $R_1$ and X are as defined above, and Y is $NR_2R_3$, wherein $R_2$ and $R_3$ are as defined above; (b) reacting said compound of formula II with an alkylating agent selected from the group consisting of an oxonium salt of the formula:

$(R)_3O^-Z^-$ and a carbonium salt of the formula:

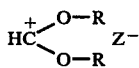

in which formulae R is methyl or ethy and $Z^-$ is the fluoroborate, hexachloroantimonate or hexafluorophosphate ion, to form a corresponding salt of formula III:

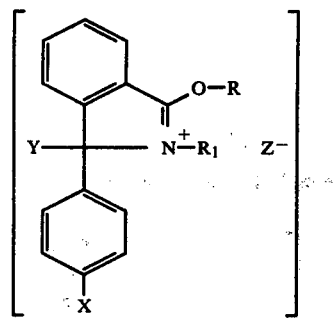

(c) reacting said salt with ethylene diamine to form an intermediate of formula IV:

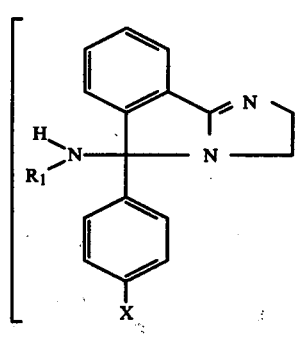

and (d) hydrolyzing said compound of formula IV to form the compound of formula I.

19. Process for the preparation of an imidazo [2,1-a] isoindole of formula I:

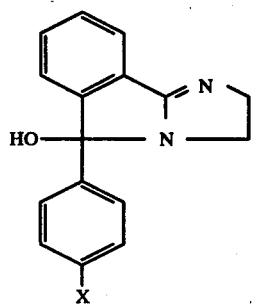

wherein X is hydrogen halogen or lower alkoxy; comprising (a) reacting a compound of formula VII:

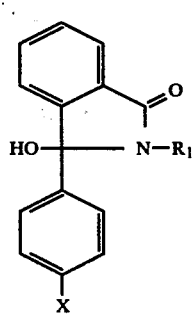

in which R₁ is lower alkyl; X is as defined above; with thionyl chloride to obtain a compound of formula VIII:

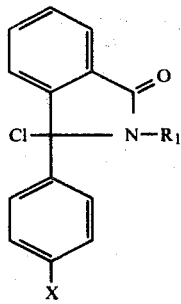

VIII wherein R₁ and X are as defined above; (b) by reacting said compound of formula VIII with:
  (i) an amine of formula HNR₂R₃ wherein R₂ and R₃ are individually lower alkyl or together are an alkylene chain of formula —(CH₂)ₙ— wherein n is 4, 5 or 6 to form an amino lactum compound of formula II; or
  (ii) an alcohol of formula R₄—OH wherein R₄ is lower alkyl or whereby an alkoxy lactam of formula II is obtained:

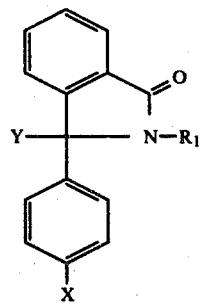

II wherein R₁ and X are as defined above, and Y is NR₂R₃ or —O—R₄, wherein R₂, R₃ and R₄ are as defined above;

(c) reacting said compound of formula II with an alkylating agent selected from the group consisting of an oxonium salt of the formula;

(R)₃O⁺Z⁻ and a carbonium salt of the formula:

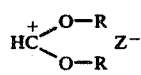

in which formulae R is methyl or ethyl, and Z³¹ is the fluoroborate, hexachlorantimonate or hexafluorophosphate ion, to form a corresponding salt of formula III:

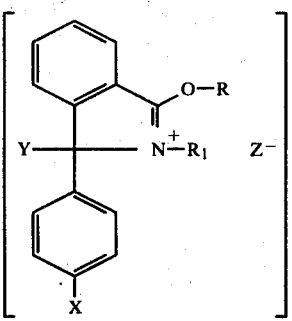

III (d) reacting said salt with ethylene diamine to form an intermediate of formula IV:

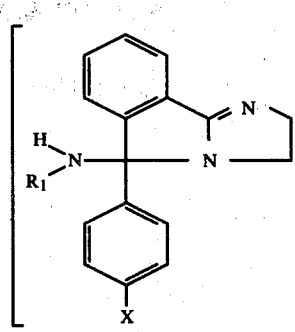

IV and (e) hydrolyzing said compound of formula IV to form the compound of formula I.

20. Process for the preparation of an imidazo [2,1-a] isoindole of formula I:

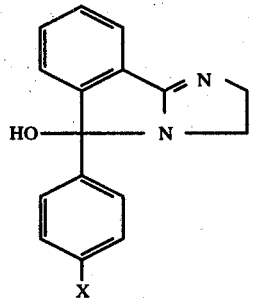

I wherein X is hydrogen, halogen or lower alkoxy; comprising (a) reacting a compound of formula VI:

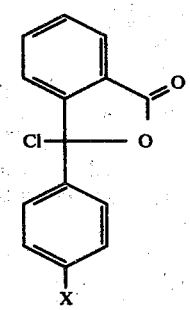

VI wherein X is as defined above; with an amine of formula H₂NR¹, wherein $R_1$ is a lower alkyl, to obtain a compound of formula VII:

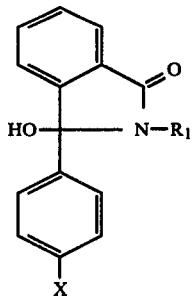

VII wherein $R_1$ and X are as defined above; with thionyl chloride to obtain a compound of formula VIII:

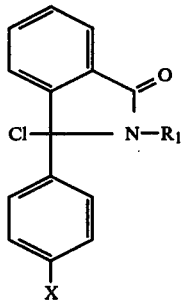

VIII wherein $R_1$ and X are as defined above; (b) reacting said compound of formula VIII with:
(i) an amine of formula HNR₂R₃ wherein $R_2$ and $R_3$ are individually lower alkyl or together are an alkylene chain of formula —(CH₂)ₙ—wherein n is 4, 5 or 6 to form an amino lactam compound of formula II; or
(ii) an alcohol of formula R₄—OH wherein $R_4$ is lower alkyl or wherein an alkoxy lactam of formula II is obtained:

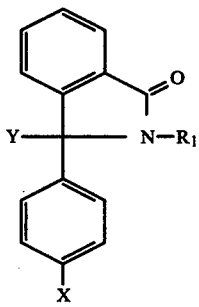

II wherein $R_1$ and X are as defined above, Y is NR₂R₃ or —O—R₄, wherein $R_2$, $R_3$ and $R_4$ are as defined above;
(c) reacting said compound of formula II with an alkylating agent selected from the group consisting of an oxonium salt of the formula:

$(R)_3O^+Z^-$ and a carbonium salt of the formula:

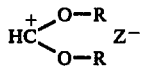

in which formulae R is methyl or ethyl, and $Z^-$ is the fluoroborate, hexachloroantimonate or hexafluorophosphate ion, to form a corresponding salt of formula III:

III (d) reacting said salt with ethylene diamine to form an intermediate of formula IV:

IV and (e) hydrolyzing said compound of formula IV to form the compound of formula I.

21. Process for the preparation of a compound of formula Ib:

Ib

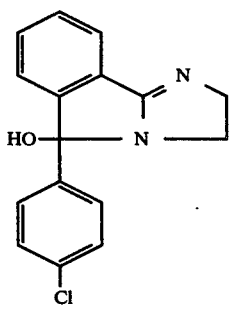

comprising (a) reacting a compound of formula IIc:

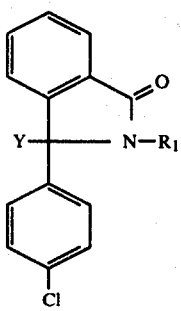

wherein $R_1$ is lower alkyl; and Y is $-NR_2R_3$, wherein $R_2$ and $R_3$ are individually lower alkyl or together are an alkylene chain of formula $-(CH_2)_n-$ where n is 4, 5 or 6, with an alkylating agent selected from the group consisting of oxonium salts of the formula:

and carbonium salts of the formula:

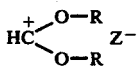

in which formulae R is methyl or ethyl; and $Z^-$ is the fluoroborate, hexachloroantimonate or hexafluorophosphate ion: to form a corresponding salt of formula IIIa:

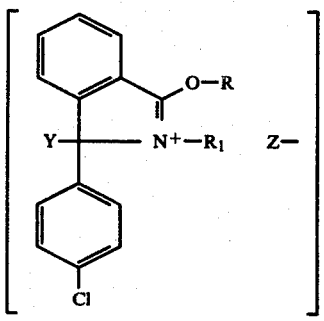

(b) reacting said salt with ethylene diamine to form an intermediate of formula IVa:

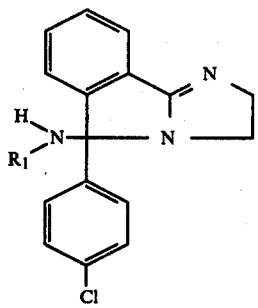

and (c) hydrolyzing said compound of formula IVa to form the compound of formula Ib.

22. The process as claimed in claim 21 in which the compound of formula IIc is alkylated under an inert gas atmosphere.

23. The process as claimed in claim 21 or 22 in which the compound of formula IIIa is reacted with ethylene diamine under an inert gas atmosphere.

24. The process as claimed in claim 21 or 22 in which said inert gas atmosphere comprises nitrogen.

25. The process as claimed in claim 21 or 22 wherein the alkylation of the compound of formula IIc is effected in the presence of an inert organic solvent.

26. The process as claimed in claim 21 or 22 wherein the alkylation of the compound of formula IIc is effected in the presence of methylene chloride.

27. The process as claimed in claim 21 or 22 wherein the alkylation of the compound of formula IIc is effected in the presence of methylene chloride and at a temperature up to the reflux temperature thereof.

28. The process as claimed in claim 21 or 22 wherein the reaction of the compound of formula IIIa with ethylene diamine is effected in the presence in an inert organic solvent.

29. The process as claimed in claim 21 or 22 wherein the reaction of the compound of formula IIIa with ethylene diamine is effected in the presence of methylene chloride.

30. The process as claimed in claim 21 or 22 wherein the reaction of the compound of formula IIIa with ethylene diamine is effected in the presence of methylene chloride and at a temperature up to the reflux temperature thereof.

31. The process as claimed in claim 21 or 22 wherein the alkylating agent is selected from the group consisting of triethyloxonium fluoroborate and dimethoxycarbonium fluoroborate.

32. The process as claimed in claim 21 for the preparation of 5-(p-chlorophenyl)-2,3-dihydro-5-hydroxy-5H-imidazo [2,1-a] isoindole, wherein 5-(p-chlorophenyl)-5-dimethylamino-2-methyl-1-isoindolinone is reacted with triethyloxonium fluoroborate, the so-obtained compound is reacted with ethylene diamine and the resulting compound is hydrolyzed with aqueous hydrochloric acid.

33. The process as claimed in claim 1 for the preparation of 5-phenyl-2,3-dihydro-5-hydroxy-5H-imidazo [2,1-a] isoindole, wherein 5-phenyl-5-dimethylamino-2-ethyl-1-isoindoline is reacted with triethyloxonium fluoroborate, the so-obtained compound is reacted with ethylene diamine and the resulting compound is hydrolyzed with aqueous hydrochloric acid.

34. The process as claimed in claim 1 for the preparation of 5-(p-chlorophenyl)-2,3-dihydro-5-hydroxy-5H-imidazo [2,1-a] isoindole, wherein 5-(p-chlorophenyl)-5-dimenthylamino2-methyl1- isoindolinone is reacted with triethyloxonium fluorborate, the so-obtained compound is reacted with ethylene diamine and the resulting compound is hydrolyzed with aqueous hydrochloric acid.

* * * * *